US010576295B2

United States Patent
Shapiro et al.

(10) Patent No.: US 10,576,295 B2
(45) Date of Patent: Mar. 3, 2020

(54) DEVICE AND METHODS FOR DIRECTING AGENTS TO THE MIDDLE EAR AND THE INNER EAR

(71) Applicant: University of Maryland, College Park, MD (US)

(72) Inventors: Benjamin Shapiro, Washington, DC (US); Didier A Depireux, Ellicott City, MD (US); Kenneth Dormer, Lynchburg, VA (US); Isaac B Rutel, Choctaw, OK (US)

(73) Assignee: University of Maryland, College Park ( * ) Notice: Subject to any disclaimer, the term of this patent is extended or adjusted under 35 U.S.C. 154(b) by 0 days.

(21) Appl. No.: 13/774,964

(22) Filed: Feb. 22, 2013

(65) Prior Publication Data

US 2014/0073835 A1 Mar. 13, 2014

Related U.S. Application Data

(63) Continuation-in-part of application No. 13/684,521, filed on Nov. 24, 2012, which is a continuation of application No. 12/712,182, filed on Feb. 24, 2010, now Pat. No. 8,316,862.

(60) Provisional application No. 61/603,076, filed on Feb. 24, 2012, provisional application No. 61/155,223, filed on Feb. 25, 2009.

(51) Int. Cl.
*A61N 2/00* (2006.01)
*A61M 37/00* (2006.01)
*A61N 2/06* (2006.01)

(52) U.S. Cl.
CPC ............. *A61N 2/002* (2013.01); *A61M 37/00* (2013.01); *A61N 2/004* (2013.01); *A61N 2/06* (2013.01)

(58) Field of Classification Search
CPC .................. A61M 37/00; A61M 31/00; A61M 2037/0007; A61F 11/00; A61F 2210/009; A61K 9/0009; A61N 2/002; A61N 2/06; A61N 1/406; A61B 5/0515
USPC ....................... 128/897, 899; 600/9, 117, 424
See application file for complete search history.

(56) References Cited

U.S. PATENT DOCUMENTS

| 6,015,377 | A | * | 1/2000 | Brown | A61N 2/06 600/9 |
| 2005/0271732 | A1 | * | 12/2005 | Seeney et al. | 424/489 |
| 2006/0213841 | A1 | * | 9/2006 | Gleich | A61N 1/406 607/103 |

FOREIGN PATENT DOCUMENTS

WO  WO 2009108478 A1 * 9/2009 ............... B82B 1/00

OTHER PUBLICATIONS

RevisionWorld, "Magnetic Fields" http://www.revisionworld.com/a2-level-level-revsion/physics/fields-0/magnetic-fields Accessed online on May 4, 2015.*
http://my.execpc.com/~rhoadley/field06.htm, Accessed online on Dec. 16, 2015.*
http://www.uq.edu.au/_School_Science_Lessons/29.173.2.GIF, Accessed online on Dec. 16, 2015.*

* cited by examiner

*Primary Examiner* — Kaylee R Wilson
(74) *Attorney, Agent, or Firm* — Lewis Brisbois Bisgaard & Smith LLP; Nigamnarayan Acharya (57) ABSTRACT

This disclosure includes a method for pushing an active agent into a patient's ear via the device. The agent can be pushed to a treatment site.

14 Claims, 5 Drawing Sheets

DEVICE AND METHODS FOR DIRECTING AGENTS TO THE MIDDLE EAR AND THE INNER EAR

PRIOR RELATED APPLICATION DATA

This application claims priority of U.S. Provisional Application Ser. No. 61/603,076, filed Feb. 24, 2012 and is a continuation in part of U.S. application Ser. No. 13/684,521, filed Nov. 24, 2012, pending, which is a continuation of U.S. application Ser. No. 12/712,182, filed Feb. 24, 2010, now U.S. Pat. No. 8,316,862, which claims priority to U.S. Provisional Patent Application Ser. No. 61/155,223, filed Feb. 25, 2009, the entire contents of which are incorporated herein by reference in their entirety.

BACKGROUND

This disclosure relates generally to the delivery of agents to the ear of a mammal. More specifically, this disclosure relates to the delivery of therapeutics agent, pharmaceutical agents, molecular agents, nucleotides, or proteins to the inner or middle ear and their use in allowing such therapeutic agents to be administered into the inner or middle ear.

SUMMARY

This disclosure includes a method for treating a patient or animal that includes providing a delivery device capable of generating a magnetic field, placing the device proximal to a patient's ear, and pushing an agent into the patient's ear via the device, wherein the therapeutic agent is pushed to a treatment site.

Additional features of the disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION

Specific embodiments provide methods, devices and systems for directing an active or therapeutic agent to and into the middle and inner ear. One exemplary embodiment is a device 10 for magnetically-assisted delivery of an active agent schematically shown in FIG. 1. One operative principle for magnetically directing (e.g., with force F) the agent (or therapeutics) associated with magnetic particles (e.g. with $Fe_3O_4$ cores), which includes magnetizable nano-particles, involves an arrangement of magnets 12, which can have a North (N) and a South (S) pole, to direct magnetic-particle formulations or agents 20 applied away from the targeted site (e.g. on the surface near the targeted site, or in the vicinity of targeted tissues) to the targeted site. Using this principle, the device with its plurality of magnets or magnetic elements can, for example, direct the agent from the fluid/gel solution to the target site.

Figure 1:
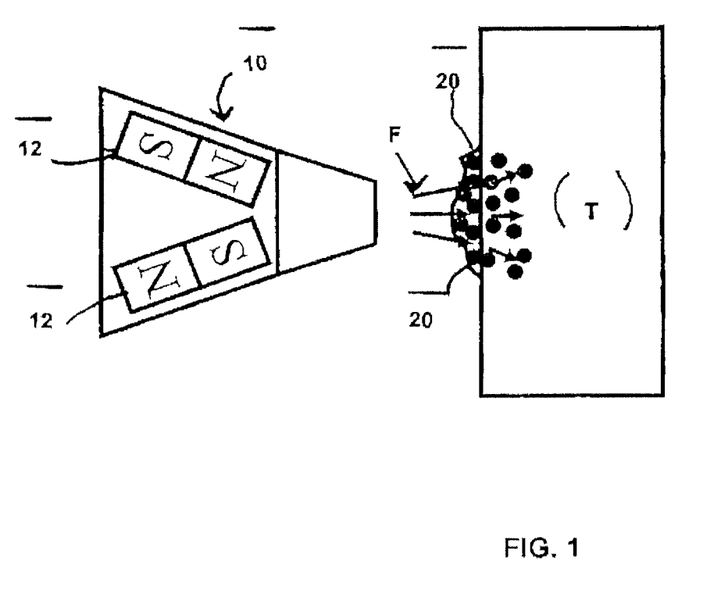
FIG. 1 shows one exemplary embodiment is a device 10 for magnetically-assisted delivery of an active agent.

In one embodiment, agents or active agents, e.g. particles associated with a therapeutic agent, can be applied away from a target site (e.g. ear canal or skin) and the device 10 can "push" or apply a force (F) on the particles to the target site (T). One embodiment includes a method for directing agents from the middle ear to the inner ear. Another embodiment includes a method for directing agents from the ear canal to the middle ear. Another embodiment includes a method for directing agents from the ear canal to the middle ear, and further directing agents to the inner ear.

In another embodiment, a method for treating a patient or animal comprises (a) placing a device proximal to the patient's ear or animal's ear, and (b) magnetically pushing an agent or active agent from the ear canal to the middle ear or from the middle ear to the inner ear. This method can be used to push an active agent from the ear canal to the middle ear and then to the inner ear. Alternatively, the active agent may be placed in the middle ear and subsequently pushed to the inner ear. Such methods can be atraumatic, can deliver a therapeutically effective amount or a concentrated dose of the agent to the middle or inner ear. In some examples, the method can effectively treat middle and inner ear diseases such as middle ear infections (also known as otitis media or glue ear), tinnitus, sudden hearing loss, and Meniere's disease by local/topical treatment.

Figure 2:
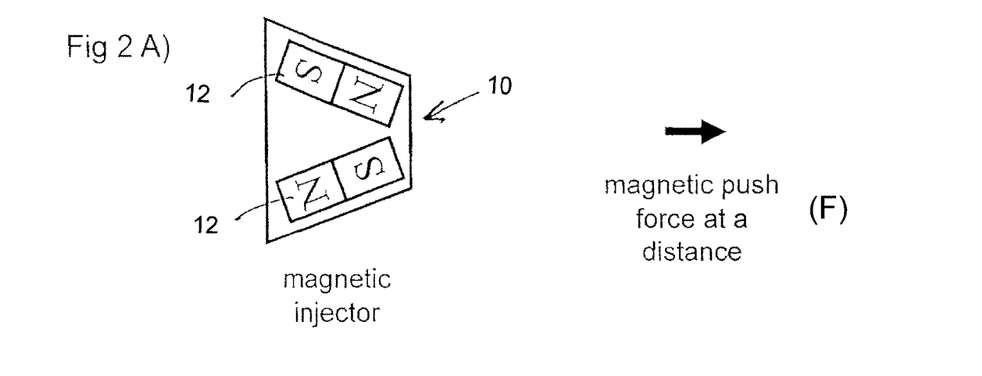
FIG. 2A shows one illustrative example of a magnetic device capable of directing or applying a force on a magnetic or magnetizable agent.
FIG. 2B illustrates one specific method to deliver active agents to the middle ear.

FIGS. 2A and 2B illustrate one specific method to deliver active agents 20 to the middle ear. As shown in FIG. 2A, the magnetic device 10 is capable of directing or applying a force F on magnetic or magnetizable agents 20 (e.g. magnetic nanoparticles coated with drugs), which can be used to direct such agents to the middle ear. To reach the inner ear without first puncturing the ear drum, the agents could be placed in the outer ear and the magnetic device or injector could be used to direct the agents first from the outer ear into the middle ear, and then from the middle ear into the inner ear. To do so, the magnetic injector could be applied once, or for a longer time period, or it could be applied multiple time in two different orientations to provide a path of the agents from outer to middle and then middle to the inner ear. The agent or agents may be placed in the outer ear or ear canal, in a liquid, gel, or via other techniques.

More particularly, FIG. 2B further illustrates the method by showing that the force F, resulting from the magnetic field, can direct the agent placed in the ear canal to the middle ear. The human ear includes three primary spaces, the outer ear canal, also known as the external acoustic meatus, the middle ear and the inner ear. The middle ear is adjacent to the outer ear canal and is separated from the outer ear canal by the tympanic membrane, also known as the ear drum. As can be seen, the magnetic device may then be held near or proximal the ear to apply magnetic forces on the agents. The magnetic forces F then "pushes" or directs the agents 20 through the ear drum (tympanic membrane) and into the middle ear. In some examples, it is possible to deliver agents to the middle ear without puncturing the ear drum.

Figure 3:
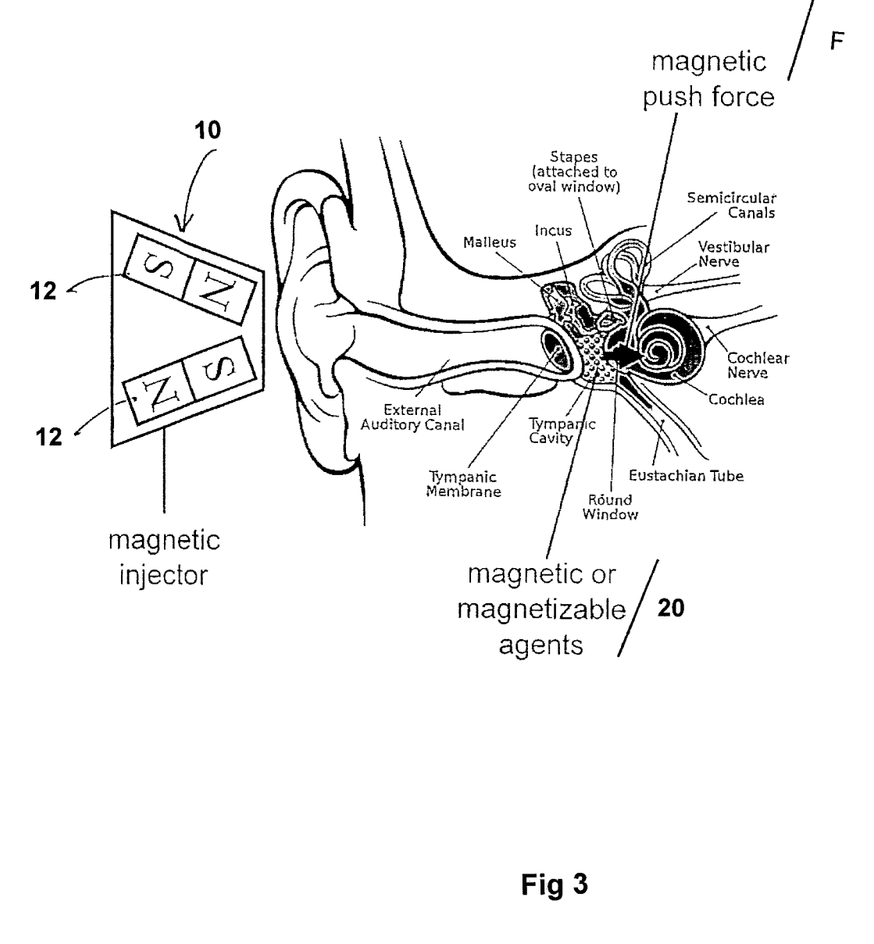
FIG. 3 illustrate a method to deliver active agents from the middle ear to the inner ear.

FIG. 3 illustrates a method to deliver active agents from the middle ear to the inner ear. In this embodiment, a magnetic device 10 can direct or apply force on magnetic or magnetizable therapeutic agents (e.g. magnetic nanoparticles coated with drugs) to direct such agents to the inner ear. The agents may be placed in the middle ear using conventional or future developed techniques, e.g., surgical techniques. The force, resulting from the magnetic field, can direct the agents placed in the middle ear to the inner ear. As can be seen, the magnetic device may then be held near the ear to apply magnetic forces on the agents. The magnetic forces F then "push" or direct the agents through the round window membrane and/or oval window membrane and into the inner ear. In some examples, it is possible to deliver effective amounts of agents to the inner ear where previously delivery of such agents was not feasible.

As can be seen from FIGS. 2A, 2B, and 3, one specific embodiment includes a method for delivering a therapeutic agent from the ear canal to the inner ear. More specifically, the active agent may be placed in the outer ear and then be pushed to the middle ear and then subsequently to the inner ear.

Another embodiment includes a device for delivering magnetizable agents to a treatment site. An arrangement of magnets creates a magnetic field that results in push forces, and these forces can be used to push in (magnetically inject) magnetic or magnetizable agents. More particularly, the device pushes outwards or magnetically injects magnetic or magnetizable carriers through tissue or materials. Specifically, it creates forces on magnetic, paramagnetic, ferrimagnetic, ferromagnetic, or superparamagnetic materials, and transports them outwards from the device (e.g., the magnetic injector). In specific examples, the device can be configured for ear treatments.

One exemplary device suitable with this method includes a device that includes a housing and a plurality of magnetic elements or magnets or magnetization that may be capable of generating magnetic fields. Typically, a single magnet can have field lines around it. The magnet can be set at an angle that creates a magnetic field along the horizontal x-axis at a desired location. A second magnet, with an opposite polarity, can be placed and angled in a configuration with respect to the first magnet so that the magnetic field is equal and opposite (along the minus x-axis) at the same desired location. The cancellation of the two fields can then create a node—a magnetic field zero or minimum. In one example, these two magnets are arranged such that the two magnetic fields overlap and can cancel at the location of the desired node point without canceling around that point. In one embodiment, a local magnetic field minimum can be created with a higher magnetic field surrounding the node. This creates magnetic forces, from regions of low to high magnetic field strength—from the node out—and thus push the magnetic or magnetizable agents away from the magnetic injection device.

Alternatively, an exemplary device suitable with this method includes a device having a housing and an electromagnet. The electromagnet may be capable of generating magnetic fields, which result in forces that can direct or push a therapeutic agent or other agent.

The plurality of magnetic elements are disposed in the housing and the magnetic field can have the effect to displace the agent from the outer to the middle ear, and can also direct it further into the inner ear, at a rate determined in part by the strength of the magnetic field. The magnetic device 10 can push therapeutic agents to the middle and/or the inner ear.

In use and practice, active agents, including magnetic or magnetizable agents, can be for example magnetic nanoparticles coated with or containing drugs or other therapy, can be delivered from an initial location to another site (e.g., a treatment site). For example, such agents can be placed on the skin or other surface as agents in a fluid (e.g. nanoparticles suspended in water), or agents in a gel, or as a powder, or as a paste, delivered in or via a flow, or by any other means that will reliably deliver them to a starting location. Then, the device is held in the vicinity of the magnetic or magnetizable agents, in such a way that the forces generated on the agents push the agents from the starting to a desired location or treatment site. This magnetic injection force can transport the agents through a barrier. For example, the starting location could be, respectively, the surface of the skin or it could be the outer or middle ear, and then the magnetic force on the agent can be used to transport them, respectively, through the skin, surface of the ear canal, or ear drum or window membranes, into the skin and middle or inner ear, respectively.

The initial placement of the agent or therapeutic agent can be accomplished in numerous ways. For example, such agents can be placed using the direct access to the outer ear in a liquid, a gel, by an atomizer (in a spray), or by other techniques. For another example, the agents may be placed in the middle ear using a syringe, scalpel, laser incision, or a tube through the ear drum (tympanic membrane).

The formulations of the pharmaceutical compounds or active agents that can be administered in connection with the methods comprise therapeutic agents, pharmaceutical agents (such as steroids, anti-inflammatory, or oto-protectant agents), molecular agents, nucleotides, or proteins.

The agents or magnetic agents or therapeutic agents can be or can include therapeutics, drugs, proteins, or gene therapy, either by having these materials themselves be magnetic (e.g. a drug molecule that is magnetic or magnetizable), by incorporating magnetic materials either on a molecular basis (e.g. drug molecules that include iron) or by being bound or attached to magnetic materials. Magnetic agents that are made by placing magnetic materials inside or attaching them to non-magnetic objects (e.g. to starch or polymer objects, to/in micelles, liposomes, viruses, bacteria, cells) can themselves be therapeutic or can further contain therapeutics, drugs, proteins, or gene therapy on their surfaces or inside them. Non-magnetic agents (such as therapeutics, drugs, proteins, or gene therapy) can also be magnetically pushed by attaching them to or containing them inside agents that are or have been made magnetic. Binding, encapsulation, coatings, and other means may be chosen to select the therapy release rates (slow or fast), release times (immediately or after a certain duration), and conditions under which release will occur (pH, osmolarity, or other parameters) to most efficaciously treat target regions or locations. The agents may be formulated into powders, suspensions, gels, sprays, lotions, or other formulations known in drug delivery.

Therapeutics and drugs can include steroids (e.g. dexamethasone, prednisone, methylprednisolone, betamethasone), prostoglandins, anti-inflammatory agents, aminoglycosides, antibiotics (e.g. glycosides) or other drugs, and nucleotide or gene therapy. They can include target-specific ligands, linkers to other moieties, polar or non-polar moieties, and elements that can be used to help transport agents across physiological barriers.

Such pharmaceutical compositions can contain a therapeutically effective amount of active ingredients, and, as may be necessary, inorganic or organic, solid or liquid pharmaceutically acceptable carriers. Pharmaceutical compositions suited for topical/local administration to the inner ear include aqueous solutions or suspensions, which may either be ready to use or require preparation prior to use (e.g. lyophilisates). Suited pharmaceutical compositions further include gels, which may be biodegradable or non-biodegradable, aqueous or non-aqueous, or micro- or nano-sphere based. Examples of such a gel include, but are not limited to, carbomers, poloxamers, alginates, hyaluronates, xyloglucans, polyesters, polysaccharides, poly(lactides), poly(glycolide) or their co-polymers PLGA, sucrose acetate isobutyrate, and glycerol monooleate, whereas the gel may be formed in situ or prior to use from solutions or suspensions. These compounds further include creams and ointments, emulsions, micro-emulsions or self-emulsifying compositions. Pharmaceutical compositions suited for enteral or parenteral administration include tablets or gelatin capsules or aqueous solutions or suspensions as described above.

The agents, including pharmaceutical compositions, may be sterilized and/or may contain adjuvants, e.g. preservatives, stabilizers, wetting agents and/or emulsifiers, salts for regulating the osmotic pressure and/or buffers, penetration enhancers, bio-adhesive agents. The pharmaceutical compositions of the invention may, if desired, contain further pharmacologically active substances, such as, but not limited to antibiotics or analgesics. They may be prepared by any of the methods, e.g. by conventional mixing, granulating, confectioning, dissolving or lyophilizing methods, and contain from about 0.01 to 100% of active ingredient.

The amount to be administered may vary, depending upon the method of administration, duration of therapy, the condition of the subject to be treated, and the severity of the ear disease. In one example, the duration of therapy may range between one minute (or less) and several hours for a single treatment, and could be administered once or multiple times over a period of days, weeks, months, or years, and may extend up to chronic treatment. The therapeutically effective amount of the compound to be delivered may range between pico-grams to milligrams.

The agent should be magnetic or magnetizable (that is associated with magnetic materials). Magnetic materials suitable for site-directed delivery can be incorporated in the coating of an oral dosage formulation or inside the oral dosage formulation and used for site-directed delivery. Alternatively, the agent can be applied topically and then delivered to the targeted site. Further, the agent can be delivered intravenously and then delivered to the targeted site.

Magnetic materials can include paramagnetic, ferrimagnetic, ferromagnetic and superparamagnetic materials (e.g. iron containing compounds), martensitic stainless steels (e.g. 400 series), iron oxides ($Fe_2O_3$, $Fe_3O_4$), neodymium iron boron, alnico (AlNiCo), and samarium cobalt ($SmCo_5$). Moreover, individual magnetic materials have been shown to possess properties that can be combined to achieve localized delivery. Ferromagnetic and superparamagnetic compounds include but are not limited to iron-containing compounds such as martensitic stainless steels (e.g. 400 series), iron and iron oxides ($Fe_2O_3$, $Fe_3O_4$).

If the agent is diamagnetic or if the magnetic material associated with the agent is diamagnetic, then the combined force from the device or system can attract the agent or associated diamagnetic material. Diamagnetic materials, all paired electrons, are slightly repelled by a magnetic field. Diamagnetic properties arise from the realignment of the electron orbits under the influence of an external magnetic field. The use of diamagnetic materials may reverse the interactions with the device or system.

In one exemplary embodiment, the magnetic material is in the form of micron-sized or sub-micron-sized particles. Such particles may be incorporated in micro or nano-carriers, optionally the micro or nano-carriers contain an active agent to be delivered. Suitable sizes for the magnetic material range from nanometers up to centimeters in cross-sectional diameter or width. In another exemplary embodiment, the magnetic material is larger than 10 nanometers in length, width, and/or diameter, and may have any shape (e.g. tubes, ellipses, etc.).

Magnetic particles may be incorporated into cells or attached to cell surfaces. In certain exemplary embodiments, magnetic particles may be fed to the target cells or temporary pores may be created in the cell membrane of the target cell by electroporation. In other exemplary embodiments, magnetic particles may be attached to the cell surface via an antibody binding to cell membrane receptors or through chemical conjugation of the magnetic particle to the cell membrane.

One or more agents may be formulated alone or with excipients or encapsulated on, in or incorporated into the microparticles or nanoparticles. Suitable agents include therapeutic, prophylactic, and diagnostic agents. These agents include organic or inorganic compounds, amino acids and proteins, sugars and polysaccharides, nucleic acids or other materials that can be incorporated using standard techniques.

In some exemplary embodiments, the magnetic fields may be provided in the form of one or more materials that are magnetic, i.e., that either exhibit a permanent magnetic field or that are capable of exhibiting a temporary magnetic field. The entire device, or selected portions thereof, may be manufactured from the one or more magnetic materials to provide a magnetic field generator. For example, a predetermined quantity of magnetite or an alloy thereof may be included in the construction of the device. Other materials may be utilized in addition to or in place of magnetite to provide the desired magnetic properties. Such materials may be temporary magnetic materials or permanent magnetic materials. Some examples of suitable magnetic materials include, e.g., magnetic ferrite or "ferrite", which is a substance consisting of mixed oxides of iron and one or more other metals, e.g., nanocrystalline cobalt ferrite. However, other ferrite materials may be used. Another example of a magnetic material is Neodymium, Cobalt, or other alloys of rare-earth elements.

In some exemplary embodiments, the agents may be biocompatible. Such agents may further be eliminated by natural processes from the middle and inner ear after treatment (e.g. via the Eustachian tube, via the lymphatic system, by metabolism, by mucosal uptake and delivery to the blood, and by other physiological means) and may eventually be cleared from the inner or middle ear. Nevertheless, if after the magnetically injected therapy has acted in the middle or inner ear (for example, after drugs have been released from the agents into the middle or inner ear), if it is desirable to remove the agents from the middle or inner ear, a magnet could be held near that ear. In reverse to the magnetic injection device, which applied injection forces, this magnet would pull the agents back out.

The term "therapeutically effective" refers to an amount of composition that is sufficient to ameliorate one or more causes or symptoms of a disease or disorder. Such amelioration only requires a reduction or alteration, not necessarily elimination of the disease or disorder. A therapeutically effective dose includes an amount effective to produce a desired effect, such as reducing or eliminating middle ear inflammation, reducing tinnitus (the perception of sound when none is present), or fully or partially restoring hearing.

Agents made from or contain magnetic, paramagnetic, ferrimagnetic, ferromagnetic, or super-paramagnetic materials. They can be of any shape or size, although spherical, elliptical, or rod shape agents are common, and they can have a variety of coatings. These agents will contain or be attached to therapeutics, or will themselves be therapeutic.

The sizes, shapes, and coatings of agents can be varied and selected based on application parameters. The magnetic force on an agent typically varies with the volume of magnetic or magnetizable materials in that agent. Thus, to increase magnetic forces, it is desirable to choose larger agents. However, larger agents may experience larger barrier resistance to motion—for the same magnetic force, it may be more difficult to move a larger agent through a biological barrier such as a tissue membrane like the ear drum or window membranes. Larger agents may also create more damage to tissue as they move through it. For this reason, there can be a tradeoff: it may be suitable to pick agents that are big enough to experience sufficient magnetic forces but small enough to move through tissue barriers easily and without causing undesirable damage. Agents may be selected to have coatings or surfaces that allow easier passage through tissue barriers.

The magnetic forces created on agents by applied magnetic fields are known to a degree. For example, it is known that the magnetic force typically scales with the volume of magnetic or magnetizable material in the agent. Forces on agents can also be measured. Thus agents can be selected to provide a desired degree of magnetic forces.

Tissue forces on agents, the forces that resist motion through tissue barriers, may be accessed. Thus we disclose carrying out tissue and animal experiments to measure tissue/barrier resistance to agent motion as a function of agent size, shape, and coating. A sample experiment is to take agents of various sizes and measure their motion through a tissue sample of specified thickness under a carefully applied magnetic field for a variety of agent shapes, sizes, and coatings. The data from such measurements can be used to determine tissue resistance to agent motion for various agent sizes, shapes, and coatings. A measurement of the motion of the agent through tissue may be used to assist in optimization. In contrast, magnetic forces on agents can be accurately predicted in many cases, but if/when they cannot, then experiments can be used instead.)

Once magnetic forces and tissue/barrier resistance have been determined, either by calculations and/or via experimental measurements, then optimal agent size, shape, and coatings are chosen to provide the optimal tradeoff between magnetic forces and tissue/barrier resistance. In one example, for directing spherical ferromagnetic nanoparticles into the inner ear over adult human distance (3-5 cm from magnetic injection device to agents placed in the middle ear), an effective sample size of nano-particles with iron cores is approximately 350 nm in diameter. In other example, magnetically injected particles as small as 20 nm and as large as 1 micrometer may be pushed by the device.

Methods and devices disclosed herein may be used with animals and humans. The term "subject," and "patient" are used interchangeably to refer to any individual who is the target of administration or treatment. The subject can be a vertebrate, for example, a mammal. Thus, the subject can be a human or veterinary patient.

EXAMPLES

The disclosure will be further described in connection with the following examples, which are set forth for purposes of illustration only.

Exemplary 1

Magnetically Directing Therapeutic Agents into the Inner Ear

The magnetic device can be used to deliver therapeutic magnetic or magnetizable agents to the inner ears of animals and humans. The magnetic or magnetizable agents were placed in the middle ear by a syringe through the ear drum. The magnetic device can then held so that magnetic forces on the agents act to transport them from the middle ear into the inner ear.

Example 2

Magnetic Device

Shown in FIGS. 1 and 2A is a magnetic injection device and a method to apply it to direct magnetic or magnetizable agents through the ear drum into the middle ear. In this example, the device consists of two or more magnetic elements that are arranged to create a magnetic field strength minimum—forces on magnetic or magnetizable agents emanate outwards from this minimum and create the pushing forces.

Example 3

Device with Two Domains

Figure 4:
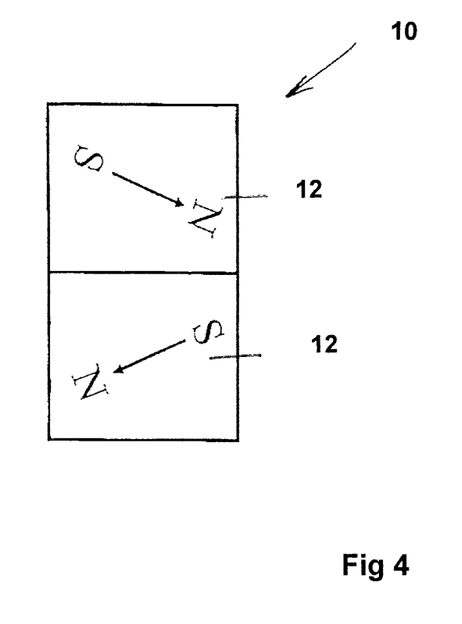
FIG. 4 shows one illustrative example of a device suitable with certain embodiments.

FIG. 4 shows a schematic diagram of a device of single magnet with at least two domains (two sub-magnets) magnetized in two different directions. This magnet was optimized to magnetically inject agents into the inner ear at adult human face-to-inner-ear distances (3-5 cm).

The orientation of the magnetization was selected to create a maximum force at a desired location. The device in rat experiments was able to inject magnetizable nano-particles into rat inner ears. The magnetization direction is the direction from "South" to "North" within each magnet or sub-magnet, and can be chosen and built to point in any desired direction. It was not necessary that North and South always correspond to the ends of a rectangular magnet, the South-to-North direction can be at an angle within the bar magnet. Suitable locations would correspond to the middle or inner ear in animal or human patients. To create maximal strength magnetic injection forces at a desired location, the magnetization directions of the elements are chosen to create the most effective magnetic field strength minimum and to place it at a desired location.

This example made it evident that other devices could have as few as two elements (two sub-magnets), or it could have a larger number of elements.

Example

Device

Figure 5:
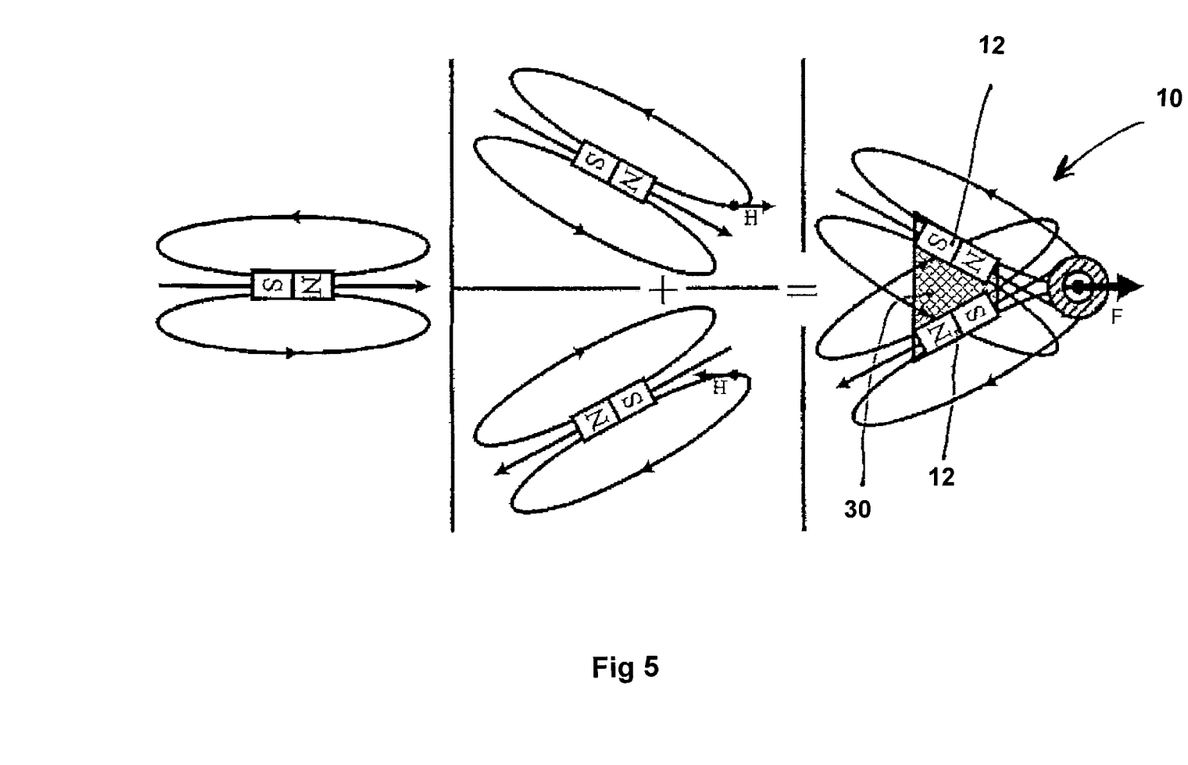
FIG. 5, one exemplary device can make use of magnetic elements or magnets that may be capable of generating magnetic fields.

As shown schematically in FIG. 5, one exemplary device 10 can make use of magnetic elements or magnets that may be capable of generating magnetic fields. In this example, these two magnets are arranged such that the two magnetic fields overlap and can cancel at the location of the desired node point without canceling around that point. The device has two magnetic elements 12 in which the first magnetic element and the second magnetic element each produce a magnetic field. The magnetic fields are represented by magnetic flux lines that extend from two magnetic poles. The plurality of magnets 12 can be placed at an angle to one another and the magnetic field lines are able to cancel out, or otherwise combine together in a fashion that creates a lower magnetic field strength, so as to form a local magnetic field minimum outside the central space 30. More particularly, the first magnetic element and the second magnetic element define a central space between the first and the second magnet.

The central space is the volume defined by the arrangement of the plurality of magnets and is the physical space between the magnets. The central space or region is defined by the physical space between the magnets that can be the least volume enclosed by a minimal convex shape, wherein the convex shape includes all material points of all the magnets. More particularly, this shape or space can be defined by common mathematical usage in that if any two points are in the volume of the space or region then the line between them is wholly included in the volume of the shape or region. A convex shape is minimal if it is the smallest convex shape that can contain all the material points of all the magnets. The central space is at least the remaining volume in such a minimal convex shape.

The first magnetic field and the second magnetic field overlap to create a combined magnetic field and create a local magnetic field strength minimum outside the central space. The combined magnetic field in front of the local minimum can produce a force on the agent. The magnetic field strength can be between 1 micro-Tesla and 8 Tesla.

Example 5

Animal Experiments

Animal experiments were conducted to test and validated device described in Example 3. The device was made by bonding two magnets together, with each magnet magnetized as shown by the "S→N" (South to North) markings. It was tested on rats, but it was held at a human adult 4 cm distance from device to inner ear distance. The device was composed of a single block of material.

The invention claimed is:

1. A method for treating a patient comprising:
   (a) providing a delivery device that generates an overall magnetic field, the device including a first magnet having a first magnetization and a first magnetic field, and a second magnet having a second magnetization and a second magnetic field, wherein the overall magnetic field is produced by the first and second magnetic fields overlapping to create a combined magnetic field and a node that is a local magnetic field strength minimum, the node being located away from the first and second magnets;
   (b) placing the device proximal to a patient's ear;
   (c) moving an agent into the patient's ear with the combined magnetic field; and
   (d) pushing the agent towards a treatment site with the combined magnetic field.

2. The method as claimed in claim 1, wherein the agent is magnetic, superparamagnetic, ferrimagnetic, ferromagnetic, or paramagnetic.

3. The method as claimed in claim 1, wherein the agent is combined with a material that is magnetic, superparamagnetic, ferrimagnetic, ferromagnetic, or paramagnetic.

4. The method as claimed in claim 1, wherein pushing the agent towards the treatment site further comprises pushing the agent away from the first and second magnets.

5. The method as claimed in claim 1, wherein the treatment site is the patient's middle ear, and wherein pushing the agent towards the treatment site includes pushing an effective amount of the agent into the patient's middle ear with the combined magnetic field.

6. The method as claimed in claim 1, wherein the treatment site is the patient's inner ear, and wherein pushing the agent towards the treatment site includes pushing an effective amount of the agent into the patient's inner ear with the combined magnetic field.

7. The method as claimed in claim 1, wherein the agent is biodegradable.

8. The method as claimed in claim 1, wherein the first and second magnets are arranged at an angle.

9. The method as claimed in claim 1, wherein moving the agent into the patient's ear includes pushing the agent into a middle ear of the patient.

10. The method as claimed in claim 9, wherein the treatment site is an inner ear of the patient, and wherein pushing the agent towards the treatment site includes pushing the agent from the middle ear to the inner ear of the patient.

11. A method to decrease inner ear or middle ear trauma in a subject while treating the subject comprising:
    (a) placing a device, that generates an overall magnetic field, proximal to a subject's ear, the device including magnetic elements each having a magnetic field, the overall magnetic field is produced by the magnetic fields of the magnetic elements overlapping to create a combined field and a node that is a local magnetic field strength minimum, the node being located away from the magnetic elements; and
    (b) pushing agents into the subject's ear with the overall magnetic field, wherein the tympanic membrane, oval window membrane or round window membrane is not materially punctured during treatment.

12. The method as claimed in claim 11, wherein magnetic elements comprise at least two magnetic elements arranged at an angle.

13. The method as claimed in claim 11, further comprising the step of placing the agents in the subject's ear canal.

14. The method as claimed in claim 11, further comprising placing the agents within the subject's middle or outer ear.

* * * * *